US005438999A

United States Patent [19]

Kikuchi et al.

[11] Patent Number: 5,438,999

[45] Date of Patent: Aug. 8, 1995

[54] ULTRASONIC TRANSDUCER

[75] Inventors: Satoko Kikuchi, Yamato; Koetsu Saitoh, Tokyo, both of Japan

[73] Assignee: Matsushita Electric Industrial Co., Ltd., Osaka, Japan

[21] Appl. No.: 228,902

[22] Filed: Apr. 18, 1994

[30] Foreign Application Priority Data

Jun. 23, 1993 [JP] Japan .................................. 5-151851

[51] Int. Cl.[6] .......................... A61B 8/00; H01L 41/10

[52] U.S. Cl. ................................. 128/662.03; 310/336

[58] Field of Search ....................... 128/662.03, 663.01; 310/334, 336; 73/642, 644

[56] References Cited

U.S. PATENT DOCUMENTS

| | | | |
|---|---|---|---|
| 4,184,094 | 1/1980 | Kopel | 128/662.03 |
| 4,205,686 | 6/1980 | Harris et al. | 128/662.03 |
| 4,446,395 | 5/1984 | Hadjicostis | 128/662.03 |
| 4,880,012 | 11/1989 | Sato | 128/663.01 |

FOREIGN PATENT DOCUMENTS

| | | |
|---|---|---|
| 61-292550 | 12/1986 | Japan . |
| 1292550 | 12/1986 | Japan . |

*Primary Examiner*—Francis Jaworski

*Attorney, Agent, or Firm*—Stevens, Davis, Miller & Mosher

[57] ABSTRACT

An ultrasonic transducer which can produce an ultrasonic image having a high resolution and a high detection depth, including a piezoelectric element having a concave surface on a side where ultrasonic waves are transmitted or received, and first and second acoustic matching layers formed on the concave surface of the piezoelectric element, the first acoustic matching layer being laid on a side near to the piezoelectric element and having a non-uniform thickness with a maximum thickness of about quarter wavelength, and the second acoustic matching layer being laid on the side near to an object to be detected and having a uniform thickness of about quarter wavelength. Thereby, the ultrasonic transducer including the acoustic matching layers having the maximum thickness set to about quarter wave length and the piezoelectric element exhibit a normal distribution type frequency characteristic over a wide range, and can allow the piezoelectric element to have an arbitrary curvature so that an ultrasonic wave can be converged at a position having an arbitrary distance.

6 Claims, 2 Drawing Sheets

ULTRASONIC TRANSDUCER

BACKGROUND OF THE INVENTION

The present invention relates to an ultrasonic transducer which is used in ultrasonic diagnosing apparatus, for transmitting and receiving ultrasonic waves.

Heretofore, studies for allowing an ultrasonic transducer to have a frequency characteristic over a wide range, and to have a structure using an acoustic lens have been made. For example, a structure disclosed in Handbook of Medical Ultrasonic Equipments, page 186. "5.3.1 Basic Structure of Ultrasonic Probe", has been well-known.

FIG. 5 shows a conventional ultrasonic transducer of this kind, which comprises a piezoelectric element 11 having a uniform thickness, at least two ultrasonic matching layers 12, 13 provided on the ultrasonic wave transmitting and receiving side (front surface side) of the piezoelectric element 11 and having a uniform quarter wave length thickness, for relaxing reflection caused by mismatching in acoustic impedance between the piezoelectric element and an object to be detected, so as to effectively radiate ultrasonic waves, a backing member 14 provided at the rear surface of the piezoelectric element 11 so as to have damping and holding functions, and an acoustic lens 15 provided at the front surface of the acoustic matching layer 13 and made of silicone rubber materials, for converging an ultrasonic beam.

The above-mentioned arrangement can have a frequency characteristic having a wide band, and further, can materialize a high resolution since the ultrasonic wave is converged thinly.

However, the conventional ultrasonic transducer having the above-mentioned arrangement has offered problems such that ultrasonic signals transmitted to or received from an object to be detected dampen so as to remarkably deteriorate its frequency characteristic in a high frequency range since the attenuation coefficient of the acoustic lens 15 made of silicone rubber materials or the like is high, and such that the sensitivity (efficiency) is remarkably deteriorated due to the attenuation through the acoustic lens 15.

SUMMARY OF THE INVENTION

The present invention is devised in order to solve the above-mentioned problems inherent to the conventional arrangement, and accordingly, one object of the present invention is to provide an ultrasonic transducer which can exhibit a frequency characteristic having a wide band without being affected by attenuation caused by the acoustic lens, and which can enhance the sensitivity (efficiency) so as to obtain an ultrasonic image having a high resolution and a deep detection depth.

To the end, according to the present invention, there is provided an ultrasonic transducer comprising a piezoelectric element having a uniform thickness and having a concave surface with an arbitrary curvature on the side where ultrasonic waves are transmitted to and received from an object to be detected, and at least one of acoustic matching layers laid on the concave surface of the piezoelectric element, at least one thereof having a non-uniform thickness while the acoustic matching layers have a maximum thickness of about one-quarter wave length.

Further, two acoustic matching layers are provided in the above-mentioned ultrasonic transducer, that is, the first acoustic matching layer laid on a side near the piezoelectric element, has a non-uniform thickness with a maximum thickness of about one-quarter wave length, and the second layer laid on the object side has a substantially uniform thickness of about quarter wave length.

Further, at least one of the acoustic matching layers can have a non-uniform thickness and can be curved in directions in which ultrasonic waves are transmitted to and received from an object to be detected, with a maximum thickness of about quarter wave length. In this case, the matching layer can be concave on the side where ultrasonic waves are transmitted to and received from an object to be detected, and the curved surface of the acoustic matching layer on the side remote from the piezoelectric element can have a curvature which is larger than the curvature of the piezoelectric element.

With this arrangement, according to the present invention, in which at least one of acoustic layers is laid so as to efficiently emit ultrasonic waves, and in which the acoustic matching layer has a maximum thickness of about quarter wave length, a gaussian shape frequency characteristic over a wide band can be obtained, and further, an ultrasonic beam can be converged without using an acoustic lens, at an arbitrary distance due to the curvature of the piezoelectric element, thereby it is possible to enhance the sensitivity of the ultrasonic transducer. Thus, a pulse-like response wave having a remarkably short wavelength can be obtained, and further, problems of deterioration in the frequency characteristic and the sensitivity (efficiency) can be eliminated, which are caused by the attenuation by an acoustic lens.

BRIEF DESCRIPTION OF THE INVENTION

These and other objects, features, advantages and uses of the present invention will be more apparent as the description proceeds when considered with the accompanying drawings in which.

DESCRIPTION OF PREFERRED EMBODIMENTS

First Embodiment

Figure 1:
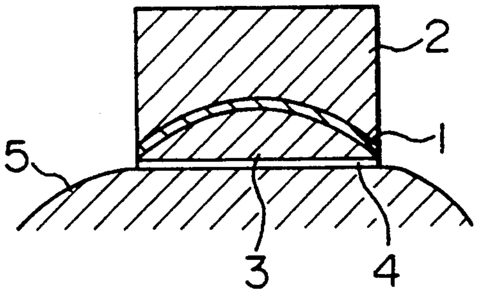
FIG. 1 is a schematic sectional view illustrating an ultrasonic transducer in a first embodiment of the present invention.
Figure 3:
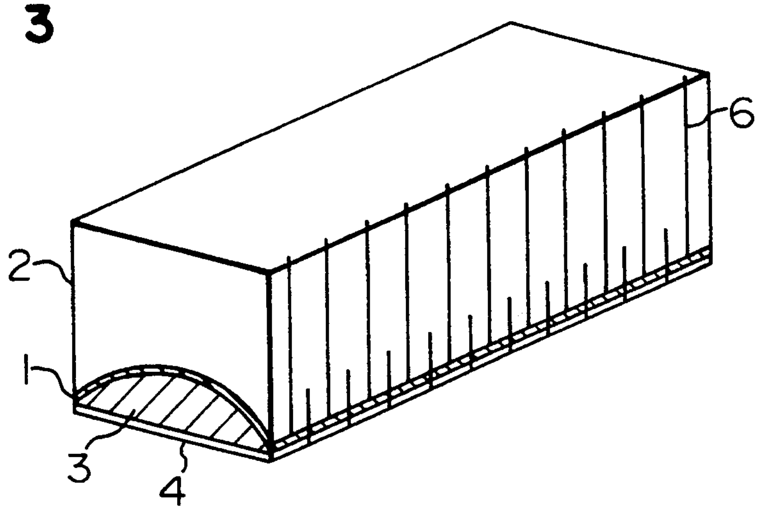
FIG. 3 is a schematic perspective view illustrating an array of ultrasonic transducers as shown in FIG. 1.

Referring to FIG. 1, an ultrasonic transducer in a first embodiment of the present invention comprises a concave piezoelectric element 1 having a uniform thickness and having an arbitrary curvature in directions in which ultrasonic waves are transmitted to and are received from an object 5 to be detected, a backing member 2 laid on one of opposite surfaces of the piezoelectric elements on the side remote from the object to be detected, a first acoustic matching layer 3 laid on the other one of the opposite surfaces of the piezoelectric element, which is a concave surface on the side where ultrasonic waves are transmitted to or received from the object to be detected, and having a flat front surface, a second acoustic matching layer 4 laid on the first acoustic matching layer 3, and lead wires 6 (refer to FIG. 3) laid at side surfaces of the backing member 2 and led from the piezoelectric element 1.

The first acoustic matching layer 3 is formed in the concave surface of the piezoelectric surface 1 so that the thickness thereof is non-uniform, having a thickest center part from which the thickness becomes smaller and smaller toward the peripheral part thereof, and accordingly, having a thinnest outermost part. Meanwhile, the second acoustic matching layer 4 has a substantially uniform thickness in its entirety, different from the first acoustic matching layer, so as to have a contact surface which is adapted to make contact with the object 5 to be detected, and which is substantially flat.

The piezoelectric element 1 is made of piezoelectric ceramic of a PZT group, $PbTiO_3$ group or the like, and for example, in the case of detection of a human body as the object 5 to be detected, the first and second acoustic matching layers 3, 4 are made of materials having an acoustic impedance of 7 to 15 MRayl, and an acoustic impedance of about 3 Mrayl, respectively. In this embodiment, materials having these impedances are used.

Figure 2:
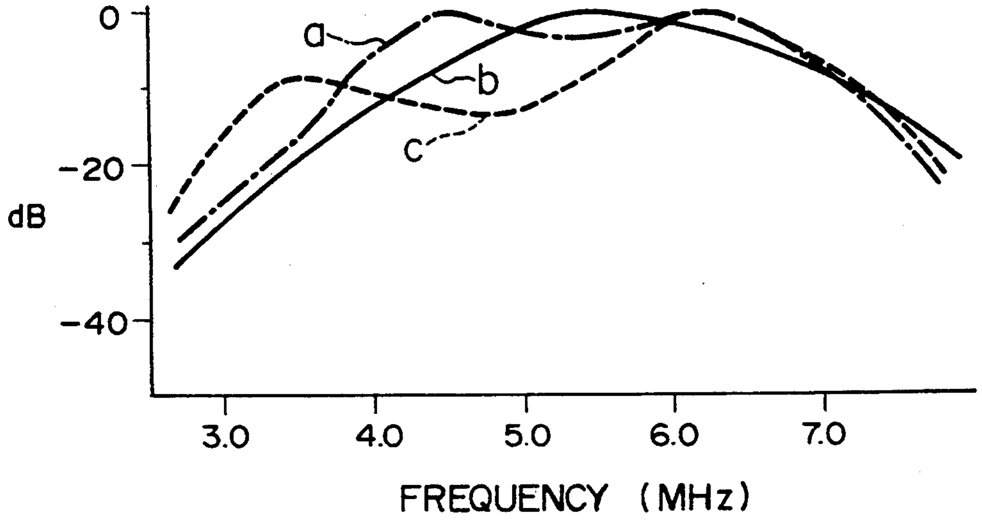
FIG. 2 is an explanatory view showing frequency characteristics of the ultrasonic transducer shown in FIG. 1.

For example, the concave piezoelectric element 1 of the $PbTiO_3$ group having a thickness with which the frequency was set to 5.0 MHz, the first acoustic matching layer 3 made of a material having an acoustic impedance of 12 MRayl and prepared by adding a filler into epoxy resin, and the second acoustic matching layer 4 made of epoxy resin having an acoustic impedance of 2.8 MRayl were used. The thickness of the thickest part (center part), that is, the maximum thickness of the first acoustic matching layer 3 was changed while the thickness of the second acoustic matching layer 4 was fixed to a uniform thickness of about quarter wave length so as to prepare a plurality of ultrasonic transducers. Then, the frequency characteristics of these transducers having the first acoustic matching layers 3 which were different from one another were measured, and the results of the measurements are shown in FIG. 2. In this figure, a, b, c are the frequency characteristics which were obtained from the first acoustic matching layers 3 having thickness of one-sixth, quarter and two-fifth wave length, respectively. Should the thickness of the first acoustic matching layer 3 be smaller than one-sixth wave length which gives the characteristic a, the frequency characteristic would deteriorate, and should it be larger than the thickness which gives the characteristic c, the frequency characteristic would deteriorate, similar to the characteristic a. From this fact, it has been found that a normal distribution type frequency characteristic over a wide band can be obtained if the thickness of the maximum thickness part of the first acoustic matching layer 3 which has a non-uniform thickness is set to about quarter wave length.

Next, the relationship between the frequency characteristic and the resolution will be briefly explained in order to give the reason why a normal distribution type frequency characteristic over a wide band is desirable for ultrasonic transducers for ultrasonic diagnosing apparatus.

Among various resolutions, the distance resolution in a direction in which ultrasonic waves are transmitted or received, is a capability of how two distal points can be resolved and displayed during transmitting and receiving of pulse waves, that is, the shorter the pulse width, the higher the resolution. In order to obtain a short pulse width, there are two methods one of which uses a high frequency, and the other of which uses a single peak characteristic (gaussian shape characteristic) having a wide band. Should the frequency characteristic be enhanced with a fixed frequency, the latter method, that is, the method having a normal distribution type frequency characteristic having a wide band, should be used.

Accordingly, it goes without saying that the characteristic having a distance resolution which is most satisfactory can be obtained by the acoustic matching layer having a thickness of quarter wave length, as given by the frequency characteristic b. Further, it is desirable that the second acoustic matching layer 4 has a thickness of about quarter wave length.

Further, since this embodiment uses the concave piezoelectric element 1 having an arbitrary curvature, an ultrasonic beam having a focus point at an arbitrary position can be formed even though an acoustic lens made of silicone rubber or the like as in a conventional one, is laid on an acoustic matching layer. Accordingly, it is of course possible to prevent deterioration of the frequency characteristic due to attenuation through an acoustic lens made of silicon rubber as in the conventional one, and further, it is possible to enhance the sensitivity (efficiency). Incidentally, in comparison a received voltage, that is, sensitivities (efficiency) between an arrangement completely identical with the conventional example and this embodiment in terms of frequency, aperture and focal distance, this embodiment exhibited a frequency characteristic which is higher than the conventional one by about 6 dB.

Although the explanation has been made in such a way that the piezoelectric element 1 is made of piezoelectric ceramic, a composite piezoelectric element made of a composite of piezoelectric ceramic and a polymer, or a PVDF piezoelectric element, can be used for obtaining a gaussian shape frequency characteristic. In this case, since the acoustic impedance of the piezoelectric element 1 becomes lower than that made of piezoelectric ceramic, the acoustic impedances of the first and second acoustic matching layers 3, 4 have to be, of course, small.

Further, although it has been explained that two acoustic matching layers 3, 4 are used in this embodiment, an ultrasonic transducer in which one acoustic matching layer or more than three acoustic matching layers are used can also exhibit a normal distribution type frequency characteristic over a wide band.

Further, although it has been explained that the second acoustic matching layer 4 has a uniform thickness and has a flat surface adapted to make contact with the object 5 to be detected, such an arrangement that the second acoustic matching layer 4 has a thickness which is non-uniform, similar to the first acoustic matching layer 3, a maximum thickness part thereof having a thickness of about one-quarter of the wavelength, and the surface of the second acoustic matching layer 4 making contact with the object 5 to be detected, is concave, can also exhibit a gaussian shape frequency characteristic over a wide band. Further, although it has been explained that the single piezoelectric element 1 is used in the ultrasonic transducer in this embodiment, the so-called array type ultrasonic transducer in which the piezoelectric element 1 is divided into several strips can also exhibit the same effects.

Second Embodiment

Figure 4:
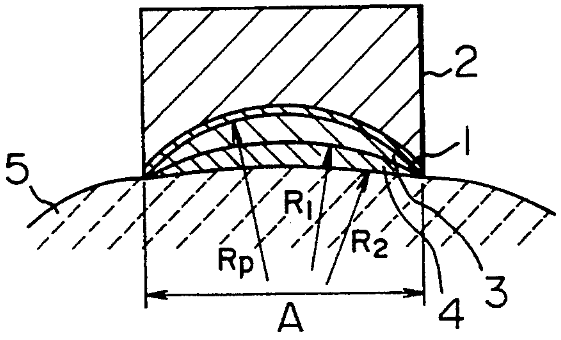
FIG. 4 is a schematic sectional view illustrating an ultrasonic transducer in a second embodiment of the present invention.
Figure 5:
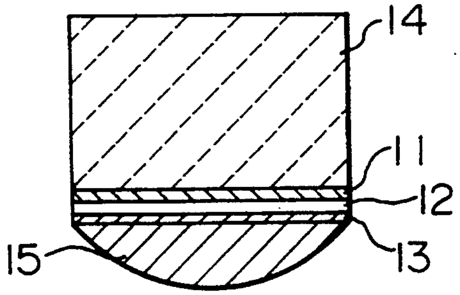
FIG. 5 is a schematic sectional view illustrating a conventional ultrasonic transducer.

Next, explanation will be made of a second embodiment with reference to the drawings. FIG. 4 is a schematic sectional view illustrating an ultrasonic transducer in the second embodiment of the present invention.

In this embodiment, as shown in FIG. 4, the ultrasonic transducer is composed of a piezoelectric element 1, a backing member 2, a first acoustic matching layer 3, and a second acoustic matching layer 4.

The radius R of curvature of the piezoelectric element 1 is determined in view of a focal point to which an ultrasonic beam is focused, and further, the aperture width A of the piezoelectric element 1 is determined, depending upon a frequency and a degree of conversion of an ultrasonic beam. Accordingly, the first acoustic matching layer 3 having a flat front surface cannot be formed on the concave surface part of the piezoelectric element 1 in a certain case, in comparison with the first embodiment in which it can be formed. That is, the height of a deepest part of the concave surface part of the piezoelectric element 1, that is equal to the maximum thickness of the first acoustic matching layer 3, cannot be set to quarter wave length. However, this problem can be solved by the arrangement shown in FIG. 4 in this embodiment.

As shown in FIG. 4, the ultrasonic wave transmitting and receiving surface of the concave piezoelectric element 1 having an arbitrary curvature radius $R_p$ is covered thereover with the first acoustic matching layer 3, excepting the outer peripheral part thereof, and further the first acoustic matching layer 3 has a concave surface shape, having a curvature radius $R_1$ so that the maximum thickness part thereof has a thickness of about quarter wave length. Further, the second acoustic matching layer 4 is laid on the first acoustic matching layer 3 and has a concave surface shape having a radius of curvature $R_2$ so that the maximum thickness part thereof has a thickness of quarter wave length, similar to the first acoustic matching layer.

For example, similar to the first embodiment, the piezoelectric element 1 is made of piezoelectric ceramic having a frequency of 5.0 MHz, and the first and second acoustic matching layers 3, 4 are made of materials having acoustic impedances of 12 MRayl (a speed of sound of 2,550 m/s) and 2.8 MRayl (a speed of sound of 2,580 m/s), respectively. If the curvature radius $R_p$ of the piezoelectric element 1 is set to 40 mm, and if the aperture diameter A is set to 10 mm, the radius $R_1$ of curvature of the first acoustic matching layer 3 becomes 67 mm in order that the maximum thickness parts of the first and second acoustic matching layers have a thickness of about quarter wavelength (which is 0.128 mm for the first acoustic matching layer 3, and which is 0.129 mm for the second acoustic matching layer 4). Further, the curvature radius $R_2$ of the second acoustic matching layer 4 becomes 218 mm. Thus, if the first and second acoustic matching layers 3, 4 have curvatures which are larger than that of the piezoelectric element 1, their maximum thickness parts can have a thickness of about quarter wave length. Further, it is noted that the maximum thickness part of the second acoustic matching layer 4 is aligned substantially with the maximum thickness part of the first acoustic matching layer 3. Further, similar to the above-mentioned first embodiment, since the piezoelectric element has a concave surface shape having an arbitrary curvature, an ultrasonic beam can be converged to a focal point having an arbitrary distance even though no acoustic lens made of silicone rubber or the like is laid on the acoustic matching layer as in the conventional one. Accordingly, it is, of course, possible to prevent deterioration of the frequency characteristic due to attenuation of an acoustic lens as in the conventional one, and further, it is possible to enhance the sensitivity (effect).

Accordingly, since an ultrasonic transducer having a gaussian shape frequency characteristic over a wide band, and a high degree of efficiency can be provided, it is possible to obtain an ultrasonic image having a high resolution and a high detection depth.

Although the explanation has been made of the piezoelectric element 1 which is made of piezoelectric ceramic, an ultrasonic transducer using a composite piezoelectric element 1 made of a composite of piezoelectric ceramic and polymer, a piezoelectric element 1 made of PVDF or the like can also give a gaussian shape frequency characteristic. However, in this case, since the acoustic impedance of the piezoelectric element 1 becomes lower than that made of piezoelectric ceramic, the first and second acoustic matching layers 3, 4 are, of course, made of materials having low acoustic impedances.

Further, although explanation has been made of the provision of the two acoustic matching layers 3, 4 in this embodiment, for example, an ultrasonic transducer using one acoustic matching layer or more than three acoustic matching layers can also exhibit a gaussian shape frequency characteristic having a wide band.

Further, although explanation has been made of the ultrasonic transducer in which each of the piezoelectric element 1 and the first and second acoustic matching layers 3, 4 in this embodiment, has only a single curvature having a center point, for example, an ultrasonic transducer in which each of them have a surface having curvatures with a plurality of center points can also exhibit a gaussian shape frequency characteristic having a wide band.

Further, although such an ultrasonic transducer that the first and second acoustic matching layers 3, 4 have respective curvatures so as to have non-uniform thicknesses has been explained in this embodiment, for example, an ultrasonic transducer in which only the first acoustic matching layer 3 is curved so as to have a non-uniform thickness while the second acoustic matching layer 4 has a uniform thickness of a quarter wave length can also exhibit a gaussian shape frequency characteristic.

Further, in this embodiment, although the ultrasonic transducer in which a single piezoelectric element 1 is used has been explained, the so-called array type ultrasonic transducer in which the piezoelectric element 1 is divided into several pieces arranged can exhibit similar effects.

As mentioned above, according to the present invention, since at least one acoustic matching layer is laid at the concave surface side of the piezoelectric element having a concave shape on the side where ultrasonic waves are transmitted and received, and has a non-uniform thickness while having a maximum thickness of quarter wave length, the ultrasonic transducer can exhibit a gaussian shape frequency characteristic over a wide range. Further, since the piezoelectric element itself is formed into such a concave shape as to have an arbitrary curvature, an ultrasonic beam can be converged, thereby making it possible to eliminate the necessity of an acoustic lens. With this arrangement, a satisfactory frequency characteristic over a wide range can be obtained while the sensitivity (efficiency) can be enhanced, and accordingly, it is possible to provide an ultrasonic image having a high resolution and a high detection depth.

What is claimed is:

1. An ultrasonic transducer comprising a piezoelectric element having a substantially uniform thickness and having a concave surface on a side where ultrasonic waves are transmitted and received, and at least one acoustic matching layer laid on the concave surface of said piezoelectric element and having a surface which is curved in a direction in which ultrasonic waves are transmitted and received, said at least one acoustic matching layer having a non-uniform thickness with a maximum thickness of about a quarter wave length.

2. An ultrasonic transducer as set forth in claim 1, wherein said at least one acoustic matching layer comprises first and second acoustic matching layers, said first acoustic matching layer is laid on a side near to said piezoelectric element and has a non-uniform thickness with a maximum thickness of about a quarter wave length, and the second acoustic matching layer is laid on a side near to an object to be detected and has a uniform thickness of about a quarter wave length.

3. An ultrasonic transducer as set forth in claim 1, wherein said surface of the at least one acoustic matching layer has a concave shape.

4. An ultrasonic transducer as set forth in claim 1, wherein a surface of the at least one acoustic matching layer on the side near to said object to be detected has a radius of curvature larger than that of said piezoelectric element, said radius of curvature of the at least one acoustic matching layer being in a range up to a value at which said surface is flat.

5. An ultrasonic transducer as set forth in claim 4, wherein a surface of the at least one acoustic matching layer on the side near to said object to be detected has a radius of curvature larger than that of said piezoelectric element, said radius of curvature of the at least one acoustic matching layer being in a range up to a value at which said surface is flat.

6. An ultrasonic transducer comprising a piezoelectric element having a substantially uniform thickness and having a concave surface on a side where ultrasonic waves are transmitted and received, and a first acoustic matching layer laid on the concave surface of said piezoelectric element and having a non-uniform thickness with a maximum thickness of about a quarter wave length and a curved shape in a direction in which ultrasonic waves are transmitted and received and a second acoustic matching layer having a non-uniform thickness, said first acoustic matching layer being laid on a side near to said piezoelectric element and said second acoustic matching layer being laid on a side near to an object to be detected and having a maximum thickness which is set at a position which substantially corresponds to a part of said first acoustic matching layer which has the maximum thickness.

* * * * *